(12) United States Patent
Eberius et al.

(10) Patent No.: US 9,701,840 B2
(45) Date of Patent: Jul. 11, 2017

(54) FLUORESCENT COMPOUNDS

(71) Applicant: BASF SE, Ludwigshafen (DE)

(72) Inventors: Karin Eberius, Grenzach (DE); Max Huegin, Ruenenberg (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/360,266

(22) Filed: Nov. 23, 2016

(65) Prior Publication Data

US 2017/0073520 A1    Mar. 16, 2017

Related U.S. Application Data

(62) Division of application No. 13/978,837, filed as application No. PCT/IB2012/050142 on Jan. 11, 2012.

(60) Provisional application No. 61/432,205, filed on Jan. 13, 2011.

(30) Foreign Application Priority Data

Jan. 13, 2011    (EP) .................................... 11150793

(51) Int. Cl.
| | | |
|---|---|---|
| *C09B 19/00* | (2006.01) | |
| *C09D 11/50* | (2014.01) | |
| *C09D 11/037* | (2014.01) | |
| *C09K 11/06* | (2006.01) | |
| *D21H 21/40* | (2006.01) | |
| *B42D 25/29* | (2014.01) | |
| *B42D 25/24* | (2014.01) | |
| *B42D 25/23* | (2014.01) | |
| *B42D 25/387* | (2014.01) | |

(52) U.S. Cl.
CPC .............. *C09B 19/00* (2013.01); *B42D 25/23* (2014.10); *B42D 25/24* (2014.10); *B42D 25/29* (2014.10); *B42D 25/387* (2014.10); *C09D 11/037* (2013.01); *C09D 11/50* (2013.01); *C09K 11/06* (2013.01); *D21H 21/40* (2013.01); *C09K 2211/1048* (2013.01)

(58) Field of Classification Search
CPC ...... C09B 19/00; C09D 11/50; B42D 15/0013
USPC ........................................................ 544/73
See application file for complete search history.

(56) References Cited

U.S. PATENT DOCUMENTS

| | | |
|---|---|---|
| 7,192,471 B2 | 3/2007 | Potrawa et al. |
| 7,740,693 B2 | 6/2010 | Potrawa et al. |
| 2006/0065154 A1 | 3/2006 | Potrawa et al. |
| 2008/0241492 A1 | 10/2008 | Maeder et al. |
| 2009/0085344 A1 | 4/2009 | Potrawa et al. |

FOREIGN PATENT DOCUMENTS

| | | |
|---|---|---|
| EP | 0 314 350 A1 | 5/1989 |
| JP | 2001-330936 A | 11/2001 |
| JP | 2008-514617 | 5/2008 |
| JP | 2010-59122 | 3/2010 |
| WO | WO 2006/036790 A1 | 4/2006 |
| WO | WO 2009/045988 A2 | 4/2009 |

OTHER PUBLICATIONS

International Search Report issued May 30, 2012 in PCT/IB2012/050142 filed Jan. 11, 2012.

Office Action issued Sep. 28, 2015, in Japanese Patent Application No. 2013-548922 (English Translation Provided).

*Primary Examiner* — Kahsay Habte

(74) *Attorney, Agent, or Firm* — Oblon, McClelland, Maier & Neustadt, L.L.P.

(57) ABSTRACT

The present invention relates to fluorescent compounds with large Stokes-shift and a process for their preparation. More particularly, the present invention relates to fluorescent compounds that are colorless. The compounds may be used in compositions for inks, paints and plastics, especially in a wide variety of printing systems and are particularly well-suited for security applications.

11 Claims, No Drawings

FLUORESCENT COMPOUNDS

CROSS REFERENCE TO RELATED APPLICATIONS

This application is a Divisional of U.S. Ser. No. 13/978,837 filed Jul. 9, 2013, allowed, which is a 35 U.S.C. §371 national stage patent application of International patent application PCT/IB2012/050142, filed on Jan. 11, 2012, published as WO/2012/095803 on Jul. 19, 2012, the text of which is incorporated by reference, and claims the benefit of the filing date of U.S. provisional application No. 61/432,205, filed on Jan. 13, 2011, and EP application no. 11150793.5, filed on Jan. 13, 2011, the text of both of which is also incorporated by reference.

The present invention relates to fluorescent compounds with large Stokes-shift and a process for their preparation. More particularly, the present invention relates to fluorescent compounds that are colourless. The compounds may be used in compositions for inks, paints and plastics, especially in a wide variety of printing systems and are particularly well-suited for security applications.

DESCRIPTION OF THE RELATED ART

Colourless materials which are highly fluorescent under UV-light (365 nm) meet a significant technical need in marking and security printing (bank notes, credit cards, identity cards, passports etc.).

A large number of organic substances belonging to the class of benzoxazinone derivatives are known for the application as fluorescent materials. Notwithstanding that large number of known compounds, the provision of products with a complex profile of properties often presents difficulties. There is a continuing demand for fluorescent pigments that are "colourless" (i.e. with the minimum absorption in the visible range of the electromagnetic spectrum), and that simultaneously meet the technical stability requirements (chemical stability, heat stability and/or light stability etc.).

A special field of application for colourless fluorescent materials regards inks for printing processes, which are used for printing currency and other security documents, also referred to as "security printing". Typical security printing processes are processes wherein an ink composition is employed that is designed to fluoresce in the yellow to green spectrum under UV light (365 nm), whilst being colourless under daylight. Fluorescent pigments for security printing are available, for example, from "Honeywell International Inc.", but virtually all of them have weaknesses in their fastness properties.

EP0314350A1 discloses compounds of formula

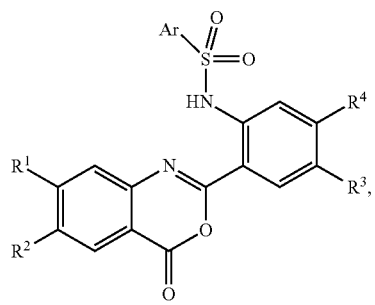

which have been found to have properties very suitable for use in fluorescent inks intended for marking security documents. $R^1$, $R^2$, $R^3$ and $R^4$ are independently H, Z or Z-substituted phenyl; and Ar is optionally Z-substituted phenyl or heterocyclyl; in which the Z's are independently selected from $C_{1-4}$alkyl, OH, $C_{1-4}$alkoxy, halogen, $NO_2$, $NH_2$, $C_{1-4}$alkylamino, di($C_{1-4}$alkyl)amino and phenyl; provided that $R^1$, $R^2$, $R^3$ and $R^4$ are not all H when Ar is alkylphenyl or alkoxyphenyl.

US2006/00651154 describes the synthesis of aryl-ureido benzoxazinones. The pigments are highly fluorescent under UV light in the range of 560 nm to about 585 nm making them useful as pigments in security inks.

WO2009045988A2 provides benzoxazinone compounds represented by the formula:

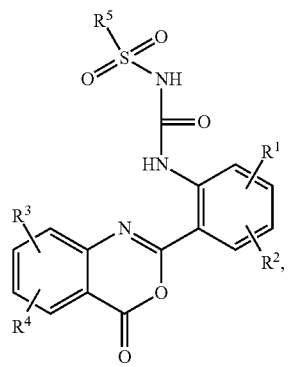

wherein each $R^1$, $R^2$, $R^3$, and $R^4$ is independently selected from hydrogen, alkyl of 1-12 carbon atoms, substituted alkyl, aryl of 6-12 carbon atoms, substituted aryl, halo, and alkoxy; and $R^5$ is selected from alkyl of 1-12 carbon atoms, substituted alkyl, aryl of 6-12 carbon atoms, substituted aryl, halo, and alkoxy; wherein each of the substituted alkyl and the substituted aryl groups have a substituent selected from alkyl, aryl, halo, and alkoxy. In addition, a mark having a benzoxazinone compound, a method for applying the mark onto an article and a process for preparing benzoxazinone compounds is disclosed.

The compounds described in the prior art may show good fastness to light.

Nevertheless, for high-end applications the benzoxazinones described in the prior art are still in need of improvement with regard to their fastness properties, e.g. fastness to solvents and bases (triethyl amine). Those properties are important in particular for applications in the field of security printing.

It has now been found, surprisingly, that certain benzoxazinone compounds exhibit high resistance against chemicals and solvents without losing their other advantages like colourlessness, good light stability and good thermal stability. They can be advantageously employed as fluorescent pigments for security printing, especially for bank notes.

SUMMARY OF THE INVENTION

In a first aspect, the invention provides compounds of formula

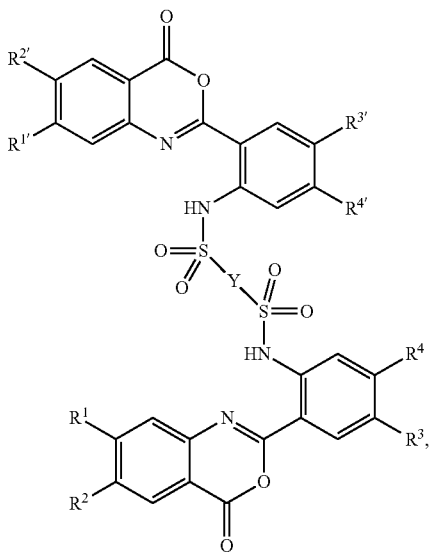
(I)

wherein
$R^1$ and $R^{1'}$ are independently of each other hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy;
$R^2$ and $R^{2'}$ are independently of each other hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_4$-$C_{24}$heteroaryl, halogen, or $C_1$-$C_{18}$alkoxy,
$R^3$ and $R^{3'}$ are independently of each other hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy,
$R^4$ and $R^{4'}$ are independently of each other hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy, or
two substituents $R^1$ and $R^2$, $R^{1'}$ and $R^{2'}$, $R^3$ and $R^4$, and/or $R^{3'}$ and $R^{4'}$ together form a group

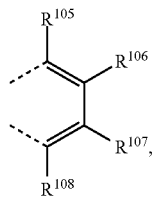

wherein
$R^{105}$, $R^{106}$, $R^{107}$ and $R^{108}$ are independently of each other H, $C_1$-$C_{18}$alkyl, $C_1$-$C_{18}$alkyl which interrupted by —O—, $C_1$-$C_{18}$alkoxy, or $C_1$-$C_{18}$alkoxy which is interrupted by —O—, and Y is a linking group.

In a further aspect, the invention provides a printing ink formulation for security printing, comprising at least one compound of the general formula I as defined above and in the following.

In a further aspect, the invention provides a security document, comprising a substrate and at least one compound of the general formula I as defined above and in the following.

In a further aspect, the invention provides a security document, obtainable by a printing process wherein a printing ink formulation is employed that comprises at least one compound of the general formula I as defined above and in the following.

DESCRIPTION OF THE INVENTION

The compounds of the general formula I have at least one of the following advantageous properties:
good fastness to chemicals, in particular fastness to bleaching with hypochlorite and fastness to solvents (like toluene, acetone or dichloromethane),
good fastness to boiling water,
good fastness to light,
colourlessness (i.e. minimal absorption in the VIS range of the spectrum (from 400 to 700 nm))
good heat stability,
high compatibility with a multiplicity of formulations, in particular printing ink formulations used in security printing.

For definition and description of fastness requirements in banknote printing see e.g "Chemical and Physical Resistance" in "Extract of the ANNEX 13 of the Technical Specification for Euro banknote production" (European Central Bank; July 2004).

In a preferred embodiment of the present invention $R^1$, $R^{1'}$, $R^2$, $R^{2'}$, $R^3$, $R^{3'}$, $R^4$ and $R^{4'}$ are independently of each other hydrogen, $C_1$-$C_8$alkoxy, halogen (especially Cl), $CF_3$, or $C_1$-$C_8$alkyl, or two substituents $R^1$ and $R^2$, $R^{1'}$ and $R^{2'}$, $R^3$ and $R^4$, and/or $R^{3'}$ and $R^{4'}$ together form a group

The compounds of general formula I can be used for security printing.

In a preferred embodiment of the present invention $R^1$ and $R^4$, $R^{1'}$ and $R^{4'}$, $R^2$ and $R^3$, and/or $R^{2'}$ and $R^{3'}$ are identical. Accordingly, compounds of formula

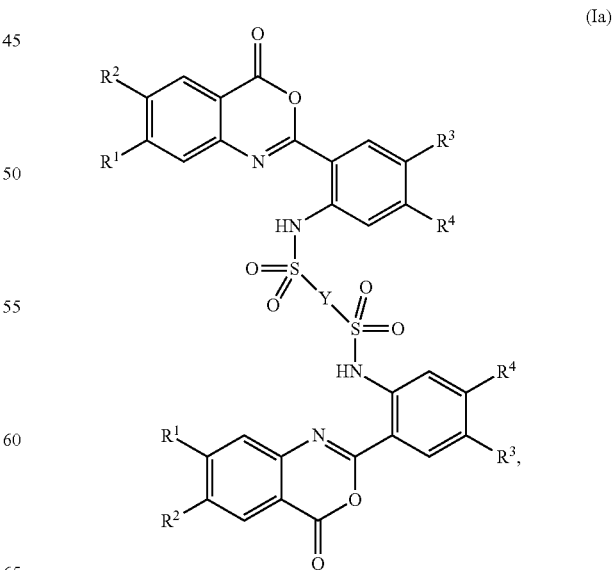

(Ia)

are preferred.

Compounds of formula Ia are more preferred, wherein
$R^1$, $R^2$, $R^3$ and $R^4$ are hydrogen;
$R^1$ and $R^4$ are hydrogen and $R^2$ and $R^3$ are a $C_{1-18}$alkyl group, especially a $C_{1-8}$alkyl group;
$R^1$ and $R^4$ are a $C_{1-18}$alkoxy group, especially a $C_{1-8}$alkoxy group, and $R^2$ and $R^3$ are hydrogen;
$R^1$ and $R^2$ and $R^3$ and $R^4$ together form a group

In a particularly preferred embodiment the present invention is directed to compounds of formula

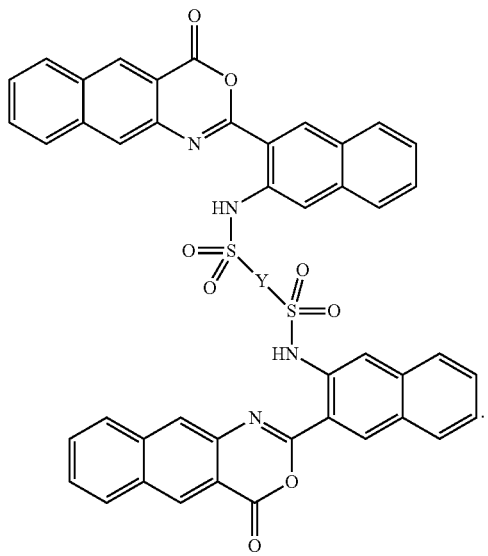

(Ib)

In a further particularly preferred embodiment the present invention is directed to compounds of formula

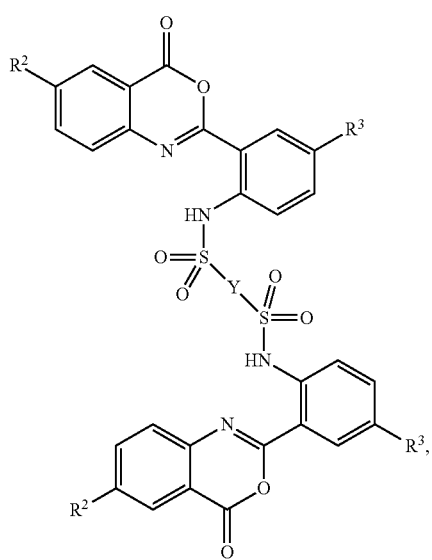

(Ic)

wherein $R^2$ and $R^3$ are independently of each other hydrogen, or $C_1$-$C_8$alkyl.

In a further particularly preferred embodiment the present invention is directed to compounds of formula

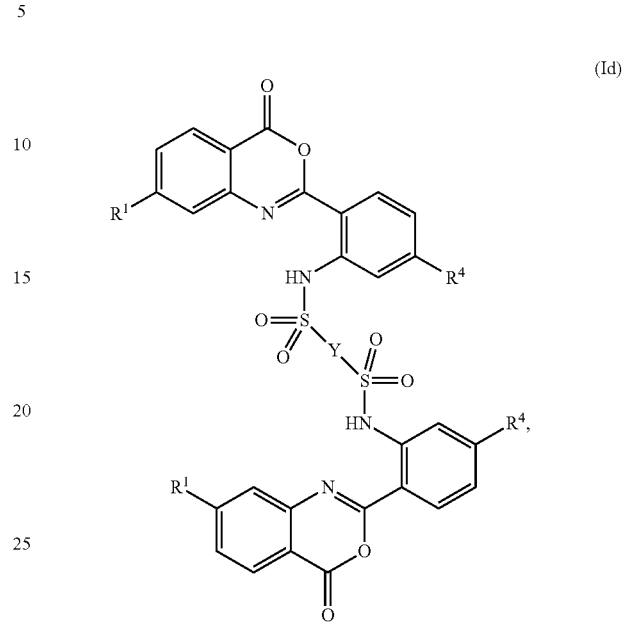

(Id)

wherein $R^1$ and $R^4$ are independently of each other $C_1$-$C_8$alkoxy.

Y is a linking group, which is not a single bond.

Y is preferably a group of formula —$(Y^1)_{n1}$—$(Y^2)_{n2}$—$(Y^3)_{n3}$—, wherein $Y^1$ and $Y^3$ are independently of each other a substituted, or unsubstituted arylene group having 6 to 30 ring carbon atoms, or a substituted or unsubstituted heteroarylene group having 3 to 30 ring carbon atoms, $Y^2$ is —O—, —S—, —$NR^{12}$—, —$SO_2$—, —C(=O)—, —$(CR^8R^9)_{n4}$—, —O—$(CR^{10}R^{11})_{n5}$—O—, $R^8$ and $R^9$ are independently of each other H, or a $C_1$-$C_8$alkyl group, $R^{10}$ and $R^{11}$ are independently of each other H, or a $C_1$-$C_8$alkyl group, $R^{12}$ is H, or a $C_1$-$C_8$alkyl group, or a $C_6$-$C_{10}$aryl group, n1 is 1, or 2, n2 is 0, or 1, n3 is 0, 1, or 2, n4 is an integer of 1 to 4 and n5 is an integer of 1 to 4.

In a preferred embodiment of the present invention Y is a group of formula —$Y^1$—, wherein $Y^1$ is a substituted, or unsubstituted arylene group having 6 to 30 ring carbon atoms, or a substituted or unsubstituted heteroarylene group having 3 to 30 ring carbon atoms.

Examples of arylene radicals are phenylene, naphthylene, phenalenylene, antracylene and phenanthrylene, which may optionally be substituted by one or more $C_1$-$C_{18}$alkyl groups, or $C_1$-$C_{18}$alkoxy groups. Preferred arylene radicals are 1,3-phenylene, 1,4-phenylene, and 3,6-naphthylene, which may optionally be substituted by one or more $C_1$-$C_{18}$alkyl groups, or $C_1$-$C_{18}$alkoxy groups.

Examples of heteroarylene radicals are 1,3,4-thiadiazol-2,5-ylene, 1,3-thiazol-2,4-ylene, 1,3-thiazol-2,5-ylene, 2,4-thiophenylene, 2,5-thiophenylene, 1,3-oxazol-2,4-ylene, 1,3-oxazol-2,5-ylene and 1,3,4-oxadiazol-2,5-ylene, 2,5-indenylene, 2,6-indenylene, especially pyrazinylene, pyridinylene, pyrimidinylene, and N-alkyl substituted carbazolylene, which may optionally be substituted by one or more $C_1$-$C_{18}$alkyl groups, or $C_1$-$C_{18}$alkoxy groups. Preferred heteroarylene radicals are 2,6-pyridinylene, 4,6-pyrimidinylene and N—$C_1$-$C_4$alkyl substituted 3,6-carbazolylene, which may optionally be substituted by one or more $C_1$-$C_{18}$alkyl groups, or $C_1$-$C_{18}$alkoxy groups.

In a further preferred embodiment of the present invention Y is a group of formula —$(Y^1)_{n1}$—$(Y^2)_{n2}$—$(Y^3)_{n3}$—, wherein $Y^1$ and $Y^3$ are independently of each other a substituted, or unsubstituted arylene group having 6 to 10 ring carbon atoms, or a substituted or unsubstituted heteroarylene group having 3 to 9 ring carbon atoms, $Y^2$ is —O—, —S—, —$NR^{12}$—, —$SO_2$—, —C(=O)—, —$(CR^8R^9)_{n4}$—, —O—$(CR^{10}R^{11})_{n5}$—O—, $R^8$ and $R^9$ are independently of each other H, or a $C_1$-$C_8$alkyl group, $R^{10}$ and $R^{11}$ are independently of each other H, or a $C_1$-$C_8$alkyl group, $R^{12}$ is H, or a $C_1$-$C_8$alkyl group, or a $C_6$-$C_{10}$aryl group, n1 is 1, or 2, n2 is 0, or 1, n3 is 1, or 2, n4 is an integer of 1 to 4 and n5 is an Integer of 1 to 4.

In said embodiment Y is preferably a group of formula —$(Y^1)_{n1}$—$Y^2$—$(Y^3)_{n3}$—, or —$(Y^1)_{n1}$—$(Y^3)_{n3}$—.

$Y^2$ is preferably a group —O—, —$SO_2$—, —$(CR^8R^9)_{n4}$—, —O—$(CR^{10}R^{11})_{n5}$—O—, more preferably a group O—, —$SO_2$—, —$CH_2$—, —$C(CH_3)_2$—, or —O—$(CH_2)_2$—O—.

$Y^1$ and $Y^3$ are preferably 1,3-phenylene, 1,4-phenylene, and 3,6-naphthylene, which may optionally be substituted by one or more $C_1$-$C_{18}$alkyl groups, or 2,6-pyridinylene and 4,6-pyrimidinylene, which may optionally be substituted by one or more $C_1$-$C_{18}$alkyl groups, or $C_1$-$C_{18}$alkoxy groups.

Examples of preferred groups of formula —$(Y^1)_{n1}$—$(Y^2)_{n2}$—$(Y^3)_{n3}$— are

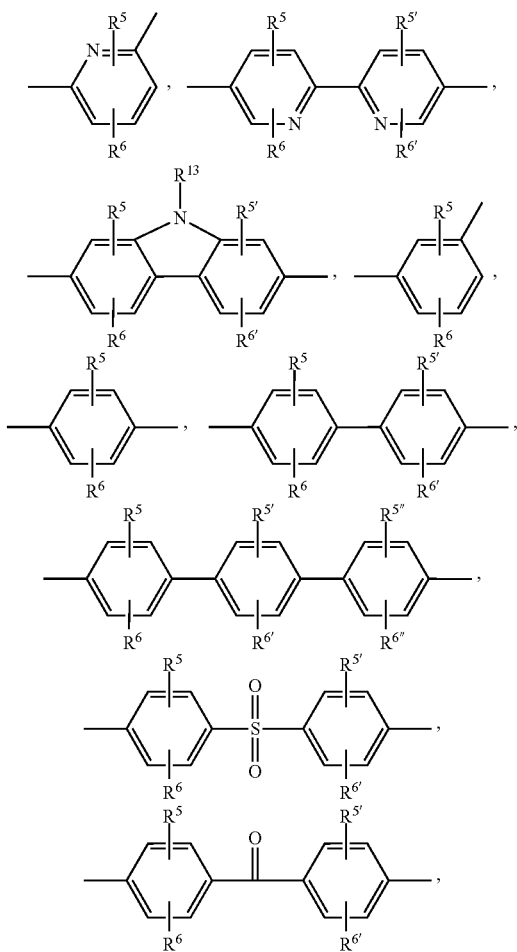

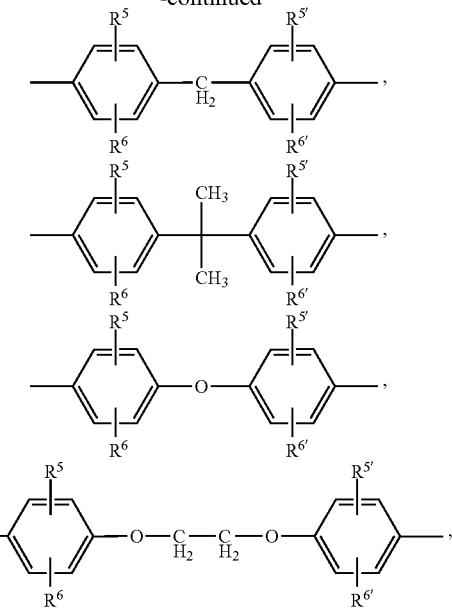

wherein $R^5$, $R^6$, $R^{5'}$, $R^{6'}$, $R^{5''}$ and $R^{6''}$ are independently of each other a $C_1$-$C_{18}$alkyl group, or a $C_1$-$C_{18}$alkoxy group and $R^{13}$ is a $C_1$-$C_8$alkyl group.

Most preferred groups of formula —$(Y^1)_{n1}$—$(Y^2)_{n2}$—$(Y^3)_{n3}$— are

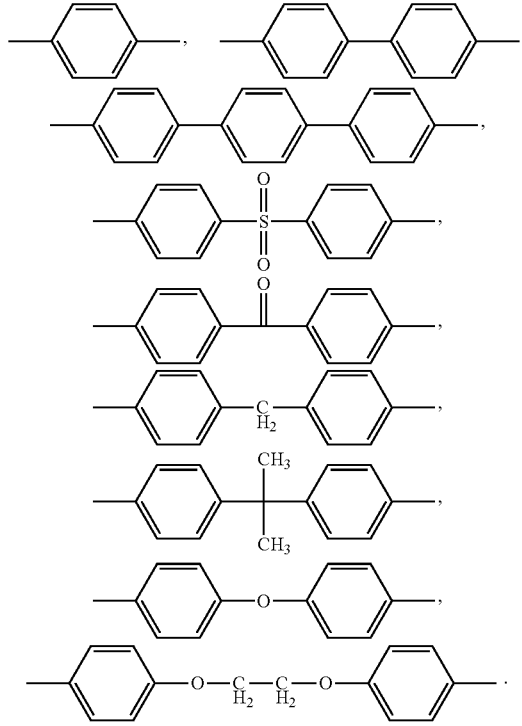

Of particular interest are the following compounds (A-1) to (A-36). Reference is made to claim 6.

In the context of the invention, the expression "halogen" denotes in each case fluorine, bromine, chlorine or iodine, preferably fluorine, chlorine or bromine, in particular fluorine or chlorine.

In the context of the present invention, the expression "alkyl" comprises straight-chain or branched alkyl groups. Alkyl is preferably $C_1$-$C_{25}$alkyl, more preferably $C_1$-$C_{18}$alkyl, most preferably $C_1$-$C_8$alkyl, in particular $C_1$-$C_4$alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The expression alkyl also comprises alkyl radicals whose carbon chains may be interrupted by one or more groups which are independently selected from —O— and —S—.

Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, amidino, $NE^1E^2$ where $E^1$ and $E^2$ are each independently hydrogen, alkyl, cycloalkyl, heterocycloalkyl, aryl or heteroaryl. Cycloalkyl, heterocycloalkyl, aryl and heteroaryl substituents of the alkyl groups may in turn be unsubstituted or substituted; suitable substituents are the substituents mentioned below for these groups.

The expression substituted alkyl group also comprises alkyl radicals that have one or more (e.g. 1, 2, 3, 4, 5 or more than 5) substituents and whose carbon chains may be interrupted by one or more groups which are independently selected from —O— and —S—.

Carboxylate and sulfonate respectively represent a metal carboxylate or metal sulfonate, or a carboxylic ester function or sulfonic ester function.

The above remarks regarding alkyl also apply to the alkyl moiety in alkoxy, alkylthio (=alkylsulfanyl), monoalkylamino and dialkylamino. $C_1$-$C_{18}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

In the context of the present invention, the term "cycloalkyl" denotes a mono-, bi- or tricyclic hydrocarbon radical having usually from 3 to 20, preferably 3 to 12, more preferably 5 to 12, carbon atoms such as cyclopropyl, cyclobutyl, cyclopentyl, cyclohexyl, cycloheptyl, cyclooctyl, cyclododecyl, cyclopentadecyl, norbornyl, bicyclo [2.2.2]octyl or adamantyl.

Substituted cycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^3E^4$ where $E^3$ and $E^4$ are each Independently hydrogen, alkyl, cycloalkyl, heterocycloalkyl, aryl or heteroaryl. In the case of substitution, the cycloalkyl groups preferably bear one or more, for example one, two, three, four or five, $C_1$-$C_6$-alkyl groups. Examples of substituted cycloalkyl groups are especially 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec.-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methylcyclooctyl, 2-, 3-, 4- and 5-ethylcyclooctyl, 2-, 3-, 4- and 5-propylcyclooctyl.

The above remarks regarding cycloalkyl also apply to the cycloalkyl moiety in cycloalkoxy, cycloalkylthio (=cycloalkylsulfanyl), monocycloalkylamino and dicycloalkylamino.

In the context of the present invention, the expression "heterocycloalkyl" comprises nonaromatic, unsaturated or fully saturated, cycloaliphatic groups having generally 5 to 8 ring atoms, preferably 5 or 6 ring atoms. In the heterocycloalkyl groups, compared to the corresponding cycloalkyl groups, 1, 2, 3, 4 or more than 4 of the ring carbon atoms are replaced by heteroatoms or heteroatom-containing groups. The heteroatoms or heteroatom-containing groups are preferably selected from —O—, —S—, —$NR^a$—, —C(=O)—, —S(=O)— and/or —S(=O)$_2$—. $R_a$ is preferably hydrogen, alkyl, cycloalkyl, heterocycloalkyl, aryl or heteroaryl.

Examples of heterocycloalkyl groups are especially pyrrolidinyl, piperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted heterocycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, amidino, $NE^5E^6$ where $E^5$ and $E^6$ are each Independently hydrogen, alkyl, cycloalkyl, heterocycloalkyl, aryl or heteroaryl. In the case of substitution, the heterocycloalkyl groups preferably bear one or more, for example one, two, three, four or five, $C_1$-$C_6$-alkyl groups.

The above remarks regarding heterocycloalkyl also apply to the heterocycloalkyl moiety in heterocycloalkoxy, heterocycloalkylthio (=heterocycloalkylsulfanyl), (monoheterocycloalkyl)amino and (diheterocycloalkyl)amino.

In the context of the present invention, the term "aryl" refers to mono- or polycyclic aromatic hydrocarbon radicals. Suitable and preferred unsubstituted and substituted aryl groups are defined in the following with regard to the substituents $R^1$, $R^{1'}$, $R^2$, $R^{2'}$, $R^3$, $R^{3'}$, $R^4$ and $R^{4'}$.

In the context of the present invention, the term "heteroaryl" (hetaryl) refers to unsubstituted or substituted heteroaromatic, mono- or polycyclic groups. Suitable and preferred unsubstituted and substituted heteroaryl groups are defined in the following with regard to the substituents $R^1$, $R^{1'}$, $R^2$, $R^{2'}$, $R^3$, $R^{3'}$, $R^4$ and $R^{4'}$.

The unsubstituted or substituted aryl groups are independently selected from unsubstituted or substituted mono- or polycyclic aromatic hydrocarbon radicals, preferably having 6 to 24 carbon atoms, more preferably having 6 to 18 carbon atoms, especially having 6 to 10 carbon atoms as ring members.

The unsubstituted or substituted aryl groups are preferably selected from unsubstituted or substituted phenyl, unsubstituted or substituted naphthyl, unsubstituted or substituted indenyl, unsubstituted or substituted fluorenyl, unsubstituted or substituted anthracenyl, unsubstituted or substituted phenanthrenyl, unsubstituted or substituted naphthacenyl, unsubstituted or substituted chrysenyl, unsubstituted or substituted pyrenyl, unsubstituted or substituted coronenyl and unsubstituted or substituted perylenyl.

The unsubstituted or substituted aryl groups are more preferably selected from unsubstituted or substituted phenyl and unsubstituted or substituted naphthyl.

The unsubstituted or substituted aryl groups are in particular selected from unsubstituted or substituted phenyl.

The substituted aryl groups may, depending on the number and size of their ring systems, have one or more (e.g. 1, 2, 3, 4, 5 or more than 5) substituents. The substituents of the substituted aryl groups are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^1E^2$ where $E^1$ and $E^2$ are each Independently hydrogen, alkyl, cycloalkyl, heterocycloalkyl, aryl or heteroaryl. The alkyl, alkoxy, alkylamino, alkylthio, cycloalkyl, heterocycloalkyl, aryl and heteroaryl substituents on the substituted aryl groups may in turn be unsubstituted or substituted. Reference is made to the substituents mentioned for these groups above and in the following.

The substituents on the substituted aryl groups are preferably selected from alkyl; alkoxy; alkyl or alkoxy whose carbon chain is interrupted by one or more nonadjacent groups selected from —O—, —S—, —$NR^a$—, —C(=O)—, —S(=O)— and/or —$S(=O)_2$—, wherein $R^a$ is hydrogen, alkyl, cycloalkyl, heterocycloalkyl, aryl or heteroaryl; haloalkyl; haloalkoxy; cycloalkyl; fluorine; chlorine; bromine; cyano and nitro.

The substituted aryl groups are preferably substituted phenyl which bears 1, 2, 3, 4 or 5 substituents. The substituted aryl groups are more preferably substituted phenyl which bears preferably 1, 2 or 3 substituents.

The substituted aryl groups are preferably selected from aryl groups substituted by at least one alkyl group ("alkaryl", also referred to as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents on the alkaryl groups may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents. The alkyl substituents on the alkaryl groups are preferably selected from $C_1$-$C_{18}$alkyl, more preferably $C_1$-$C_8$alkyl and most preferably $C_1$-$C_4$alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The unsubstituted or substituted heteroaryl groups are independently selected from unsubstituted or substituted heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The heteroaryl groups have preferably 5 to 18, e.g. 5, 6, 8, 9, 10, 11, 12, 13 or 14, ring atoms.

Unsubstituted or substituted monocyclic heteroaryl groups are preferably selected from unsubstituted or substituted 5- or 6-membered heteroaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Unsubstituted or substituted polycyclic heteroaryl groups preferably have 2, 3, 4 or more than 4 fused rings. The fused-on rings may be aromatic, saturated or partly unsaturated. Examples of polycyclic heteroaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

The substituted hetaryl groups may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^3E^4$ where $E^3$ and $E^4$ are each independently hydrogen, alkyl, cycloalkyl, heterocycloalkyl, aryl or heteroaryl. Halogen substituents are preferably fluorine, chlorine or bromine.

The substituents on the substituted hetaryl groups are preferably selected from alkyl; alkoxy; alkyl or alkoxy whose carbon chain is interrupted by one or more nonadjacent groups selected from —O—, —S—, —$NR^b$—, —C(=O)—, —S(=O)— and/or —$S(=O)_2$—, wherein Rb is hydrogen, alkyl, cycloalkyl, heterocycloalkyl, aryl or heteroaryl; haloalkyl; haloalkoxy; cycloalkyl; fluorine; chlorine; bromine; cyano and nitro.

The substituted hetaryl groups are preferably selected from heteroaryl groups substituted by at least one alkyl group. Alkyl substituted heteroaryl groups may, depending on the size of the aromatic ring system, have one or more (e.g. 1, 2, 3, 4, 5, 6, 7, 8, 9 or more than 9) alkyl substituents. The alkyl substituents on the heteroaryl groups may be unsubstituted or substituted. In this regard, reference is made to the following statements regarding unsubstituted and substituted alkyl. In a preferred embodiment, the heteroaryl groups have exclusively unsubstituted alkyl substituents. The alkyl substituents on the hetaryl groups preferably selected from $C_1$-$C_{18}$alkyl, more preferably $C_1$-$C_8$alkyl and most preferably $C_1$-$C_4$-alkyl.

Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

Compounds of the formula

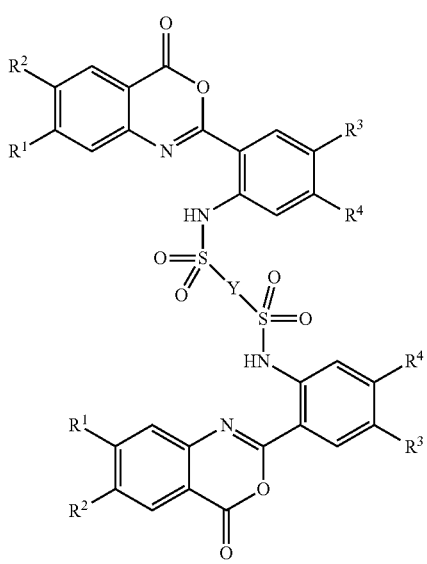

(Ia)

can be obtained by reacting a compound of formula

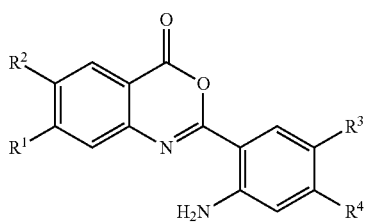

(II)

with a compound of formula

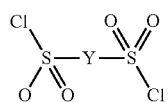

(III)

in a solvent in the presence of a base, wherein Y, $R^1$, $R^2$, $R^3$ and $R^4$ are as defined above.

In addition, compounds of formula I can be obtained by condensation of compounds of formula II with compounds of formula III in a solvent in the presence of a base, wherein intermediates of formula

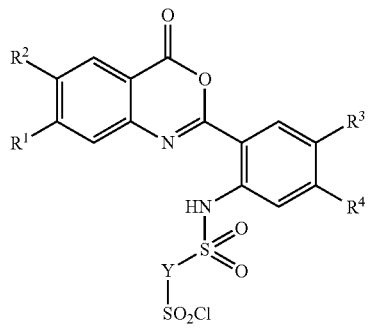

(VI)

are obtained, which are reacted with compounds of formula

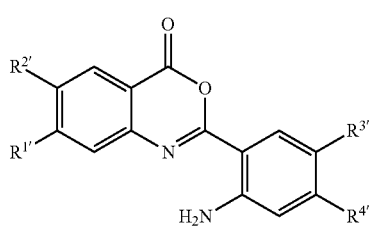

(II')

(condensation of 1 equivalent of a compound of formula II with 1 equivalent of a compound of formula III in 25 equivalents of pyridine and after isolation of intermediate VI condensation with a compound of formula II').

Examples of preferred bases are 1,8-diazabicyclo[5.4.0] undec-7-ene (DBU), 1,5-diazabicyclo[4.3.0]non-5-ene (DBN), (Hünig Base), trialkylamines, such as, for example, triethyl amine, or diisopropylethyl amine, and pyridine.

The base, such as, for example, pyridine, can also function as solvent.

Preferred solvents are dipolar aprotic solvents, such as, for example, monoethylene glycol dimethyl ether (monoglyme), diethylene glycol dimethyl ether (diglyme), triethylene glycol dimethyl ether (triglyme) and tetraethylene glycol dimethyl ether (tetraglyme) dioxane, dimethylsulfoxide (DMSO), sulpholane, dimethylacetamide, 1,3-dimethylimidazolin-2-one, N-methylpyrrolidone, benzonitrile, N,N-dimethylformamide (DMF), tetrahydrofuran (THF), or acetonitrile.

Preferably, pyridine is used as base and solvent, or triethyl amine is used as base and THF as solvent. If pyridine is used as base and solvent, 5-20 parts of compound of formula II, 2.5-12 parts of compound of formula III and 68-92.5 parts of pyridine are employed, wherein the amounts of compound of formula II, compound of formula III and pyridine add up to 100 parts.

The reaction is conducted at temperatures ranging from 0° C. to reflux temperature of the solvent, more preferably at 22 to 115° C. Very particular preference is given to 40 to 50° C.

Compounds of formula II and III are either commercially available or may be prepared via synthetic methods well known in the art.

Condensation of one equivalent of substituted anthanilic acid IV with one part of anthranilic acid chloride V results in a compound of formula II.

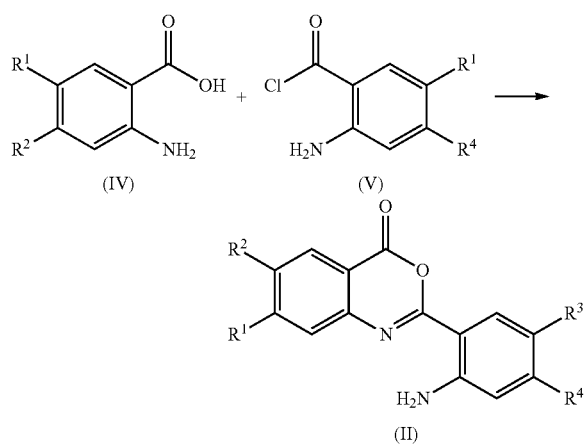

Compounds of formula V can be obtained by condensation of commercially available anthranilic acid derivatives with thionyl chloride (2 equivalents of anthranilic acid and 3 equivalents of thionyl chloride are reacted in 12 equivalents of pyridine).

The compounds of formula I can also be used in the form of a mixture, comprising at least one compound of formula I and at least one further fluorescent compound different from compounds of I. Suitable further fluorescent compounds are in principle all known classes of fluorescent compounds that are compatible with the compounds of formula I. Suitable further fluorescent compounds are e.g. coumarins, stilbenes, benzoxazole, benzthiazole, benzodiazole, bipyridyl derivatives, rare earth metal complex compounds, colourless inorganic fluorescent materials as well as daylight fluorescent organic materials, e.g. perylenes, xanthenes, maleimides, naphtalimides, Pigment Yellow 101 (=2,2'-dihydroxynaphtaldazine (Lumogen® Gelb S 0790)), Irgazin Gelb GF (1,2,3,4-tetrachloro-benzo[4,5]imidazo[2,1-a]isoindol-11-one).

The compounds of formula I can be generally used in a concentration of from 10 ppm to 25%, preferably 100 ppm to 10%, depending on the chosen application.

The compounds of formula I and fluorescent mixtures are especially suitable for security printing.

Security printing is the field that deals with the printing of items such as currency, passports, tamper-evident labels, stock certificates, postage stamps, identity cards, etc. The main goal of security printing is to prevent forgery, tampering or counterfeiting.

In the field of automated banknote processing, fluorescence plays an important role. Most of the actually circulating currency carries not only visibly coloured printings, but also specific features which are only detectable by irradiation with UV light. Generally, these fluorescent features are implemented for use by automatic currency processing equipment, in banking and vending applications (automatic teller machines, automatic vending machines, etc.), in order to recognize a determined currency bill and to verify its authenticity, in particular to discriminate it from replicas made by colour copiers.

All security documents are required to have good stability and durability. In the case of bank notes, these requirements are extreme, as bank notes are subjected to toughest use conditions by the public—they are subjected to material stress by folding, crumpling etc., subjected to abrasion, exposed to weather, exposed to bodily fluids such as perspiration, laundered, dry-cleaned, ironed etc.—and, after having been subjected to this, are expected to be as legible as when they started. Furthermore, it is essential that the documents nevertheless should have a reasonable life time, ideally of some years, despite suffering the afore-mentioned conditions. During this time, the documents, and thus the inks on them (including invisible security markings), should be resistant to fading or colour change. Hence, any ink used in a security printing process should, when cured, be robust, water-resistant, resistant to various chemicals and flexible. Moreover, as certain states are moving away from the use of paper as the substrate for bank notes, the employed printing ink formulations should be useable on plastics as well as paper. It has now been found that the compounds of the formula I because of their unique application properties are especially suitable for printing ink formulations that are employed for security printing and in particular for bank notes.

In security printing, the compound of the formula I is added to a printing ink formulation. Suitable printing inks are water-based, oil-based or solvent-based printing inks, based on pigment or dye, for inkjet printing, flexographic printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing and letterpress printing are usually formulated as high-viscosity paste printing inks, whereas printing inks for flexographic printing and intaglio printing are usually formulated as liquid printing inks with comparatively low viscosity.

In the context of the present invention, the expression "printing ink" also encompasses formulations that in addition to at least one compound of the formula I comprise a colorant. The expression "printing ink" also encompasses printing lacquers that comprise no colorant.

The printing ink formulation for security printing according to the invention preferably comprises a) at least one compound of the formula I as defined above,
b) a polymeric binder,
c) a solvent,
d) optionally at least one colorant, and
e) optionally at least one further additive.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"-Ullmann's Encyclopedia of Industrial Chemistry, Sixth Edition, 1999 Electronic Release. A formulation of an IR-absorbing intaglio ink formulation is described in US20080241492A1. The disclosure of the afore-mentioned documents is incorporated herein by reference.

The printing ink formulation according to the invention contains in general from 0.0001 to 25% by weight, preferably from 0.001 to 15% by weight, in particular from 0.01 to 5% by weight, based on the total weight of the printing ink formulation, of component a).

The compounds of the formula I are present in the printing ink formulation in dissolved form or in solid form (in a finely divided state).

The printing ink formulation according to the invention contains in general from 5 to 74% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by G. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 1 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvent are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains in from 0 to 25% by weight, more preferably from 0.1 to 20% by weight, in particular from 1 to 15% by weight, based on the total weight of the printing ink formulation, of a colorant d).

Suitable colorants d) are selected conventional dyes, and in particular conventional pigments. The term "pigment" is used in the context of this invention comprehensively to identify all pigments and fillers, examples being colour pigments, white pigments, and Inorganic fillers. These include inorganic white pigments such as titanium dioxide, preferably in the rutile form, barium sulfate, zinc oxide, zinc sulfide, basic lead carbonate, antimony trioxide, lithopones (zinc sulfide+barium sulfate), or colored pigments, examples being iron oxides, carbon black, graphite, zinc yellow, zinc green, ultramarine, manganese black, antimony black, manganese violet, Paris blue or Schweinfurt green. Besides the Inorganic pigments the printing ink formulation of the invention may also comprise organic colour pigments, examples being sepia, gamboge, Cassel brown, toluidine red, para red, Hansa yellow, indigo, azo dyes, anthraquinonoid and indigoid dyes, and also azo, dioxazine, quinacridone, quinophthalone, diketopyrrolopyrrole, phthalocyanine, isoindoline, isoindolinone, and metal complex pigments. Also suitable are synthetic white pigments with air inclusions to increase the light scattering, such as the Rhopaque® dispersions. Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains in from 0 to 25% by weight, more preferably from 0.1 to 20% by weight, in particular from 1 to 15% by weight, based on the total weight of the printing ink formulation, of at least one component e).

Suitable additives (component e) are selected from plasticizers, waxes, siccatives, antistatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

In particular, the printing ink formulation for security printing according to the invention preferably contains
a) 0.0001 to 25% by weight of at least one compound of the formula I,
b) 5 to 74% by weight of at least one polymeric binder,
c) 1 to 94.9999% by weight of at least one a solvent,
d) 0 to 25% by weight of at least one colorant, and
e) 0 to 25% by weight of at least one further additive,
wherein the sum of components a) to e) adds up to 100%.

The printing ink formulations according to the invention are advantageously prepared in a conventional manner, for example by mixing the individual components. As mentioned earlier, the compound of the formula I is present in the printing ink formulations in a dissolved or finely divided solid form. Additional colorants may be employed in the printing ink formulation of the invention or in a separate ink formulation. When additional colorants are to be employed in a separate formulation, the time of application of the printing ink formulation according to the invention is usually immaterial. The printing ink formulation according to the invention can for example be applied first and then be overprinted with conventional printing inks. But it is also possible to reverse this sequence or, alternatively, to apply the printing ink formulation according to the invention in a mixture with conventional printing inks. In every case the prints are readable with suitable light sources.

Primers can be applied prior to the printing ink formulation according to the invention. By way of example, the primers are applied in order to improve adhesion to the substrate. It is also possible to apply additional printing lacquers, e.g. in the form of a covering to protect the printed image. Additional printing lacquers may also be applied to serve aesthetic purposes, or serve to control application-related properties. By way of example, suitably formulated additional printing lacquers can be used to influence the roughness of the surface of the substrate, the electrical properties, or the water-vapour-condensation properties. Printing lacquers are usually applied in-line by means of a lacquering system on the printing machine employed for printing the printing ink formulation according to the invention.

The printing ink formulations according to the invention are also suitable for use in multilayer materials. Multilayer materials are e.g. composed of two or more plastics foils, such as polyolefin foils, metal foils, or metallised plastics foils, which are bonded to one another, by way of example, via lamination or with the aid of suitable laminating adhesives. These composites may also comprise other functional layers, such as odour-barrier layers or water-vapour barriers.

The following examples are included for illustrative purposes only and do not limit the scope of the claims. Unless otherwise stated, all parts and percentages are by weight.

EXAMPLES

Example 1

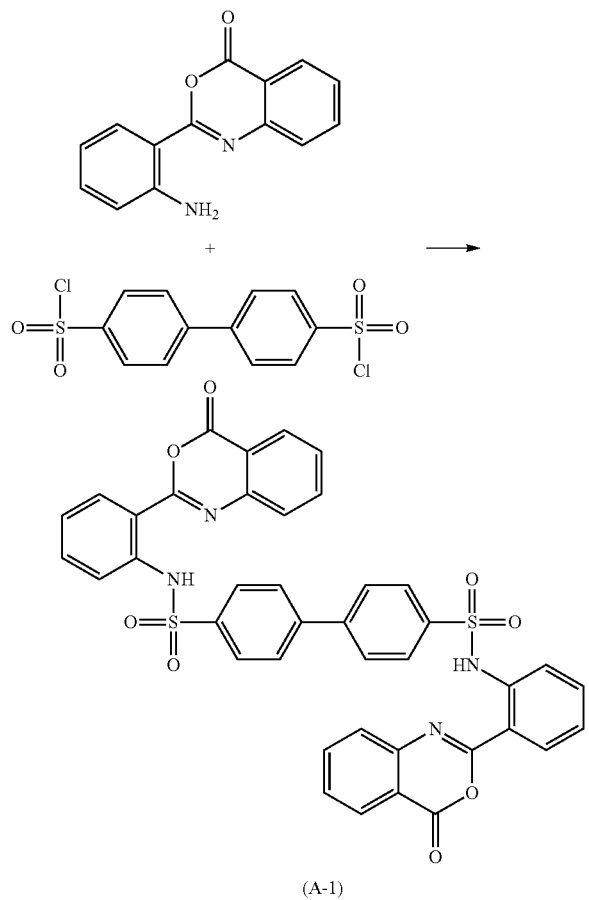

(A-1)

18.5 parts of anthanilic acid are dissolved in 60 parts of pyridine at 22° C. Over a period of 2.5 hours 21.5 parts of thionyl chloride are added at 1-5° C. to the stirred solution. After a further hour of stirring the mixture is added to 28 parts of water. The mixture is heated for 30 minutes at 80° C. The mixture is filtered and washed with water to give 2-(2-aminophenyl)-4H-3,1-benzoxazin-4-one as a yellow solid (81% yield).

19.9 parts of 2-(2-aminophenyl)-4H-3,1-benzoxazin-4-one are dissolved in 68.1 parts of pyridine at 22° C. Over a period of 5 minutes 12.0 parts of biphenyl-4,4-disulphonyl chloride are added at 40° C. to the stirred solution. After a 2.0 hour of stirring the mixture is filtered and washed with water to give the product as yellow solid (54% yield).

Example 2

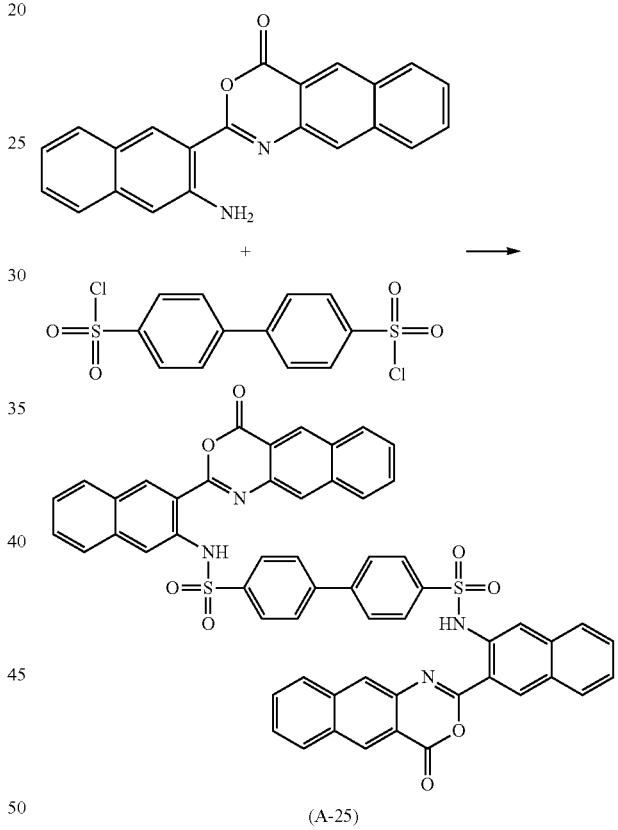

(A-25)

24.3 parts of 3-amino-2-naphthoic acid are dissolved in 44.2 parts of pyridine at 22° C. Over a period of 2.5 hours 31.5 parts of thionyl chloride are added at 1-5° C. to the stirred solution. After a further hour of stirring the mixture is added to 28 parts of water. The mixture is heated for 30 minutes at 80° C. The mixture is filtered and washed with water to give 2-(3-amino-naphthalen-2-yl)-naphtho[2,3-d][1,3]oxazin-4-one2-as a yellow solid (28% yield).

5.6 parts of 2-(3-amino-naphthalen-2-yl)-naphtho[2,3-d][1,3]oxazin-4-one are dissolved in 91.6 parts of pyridine at 22° C. Over a period of 5 minutes 2.8 parts of biphenyl-4,4-disulphonyl chloride are added at 40° C. to the stirred solution. After a 2.0 hour of stirring the mixture is filtered and washed with water to give the product as yellow solid (27% yield).

The compounds shown in the Table below are prepared in analogy to compounds A-1 and A-25.
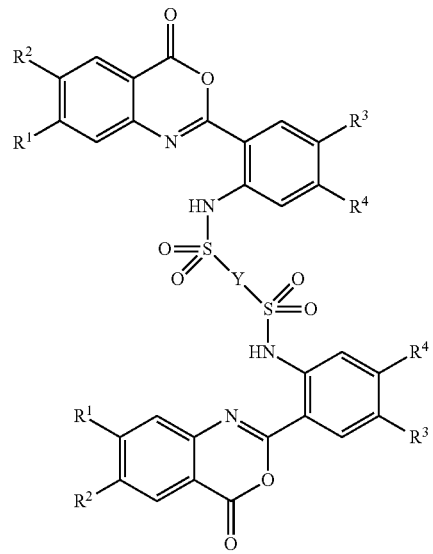
| Compound | R¹ | R² | R³ | R⁴ | Y | Fluorescence colour[4] |
|---|---|---|---|---|---|---|
| A-1 | H | H | H | H | —C₆H₄—C₆H₄— (biphenyl) | YG |
| A-2 | H | H | H | H | —C₆H₄— (phenylene) | G |
| A-3 | H | H | H | H | —C₆H₄—SO₂—C₆H₄— | YG |
| A-4 | H | H | H | H | —C₆H₄—C(O)—C₆H₄— | YG |
| A-5 | H | H | H | H | —C₆H₄—CH₂—C₆H₄— | YG |
| A-6 | H | H | H | H | —C₆H₄—C(CH₃)₂—C₆H₄— | Y |
| A-7 | H | H | H | H | —C₆H₄—O—C₆H₄— | G—YG |
| A-8 | H | H | H | H | —C₆H₄—Y—C₆H₄—[1] | YG |
| A-9 | H | CH₃ | CH₃ | H | —C₆H₄—C₆H₄— (biphenyl) | Y |

-continued
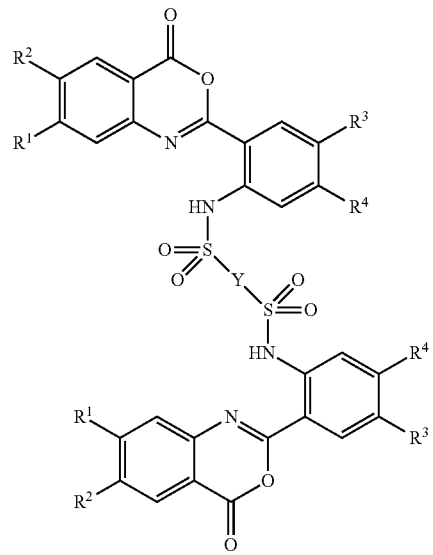
| Compound | R¹ | R² | R³ | R⁴ | Y | Fluorescence colour[4] |
|---|---|---|---|---|---|---|
| A-10 | H | CH₃ | CH₃ | H | —⟨C₆H₄⟩— (1,4-phenylene) | YG |
| A-11 | H | CH₃ | CH₃ | H | —⟨C₆H₄⟩—SO₂—⟨C₆H₄⟩— | Y |
| A-12 | H | CH₃ | CH₃ | H | —⟨C₆H₄⟩—C(O)—⟨C₆H₄⟩— | Y |
| A-13 | H | CH₃ | CH₃ | H | —⟨C₆H₄⟩—CH₂—⟨C₆H₄⟩— | YG |
| A-14 | H | CH₃ | CH₃ | H | —⟨C₆H₄⟩—C(CH₃)₂—⟨C₆H₄⟩— | Y |
| A-15 | H | CH₃ | CH₃ | H | —⟨C₆H₄⟩—O—⟨C₆H₄⟩— | G—YG |
| A-16 | H | CH₃ | CH₃ | H | —⟨C₆H₄⟩—Y—⟨C₆H₄⟩—[1] | G—YG |
| A-17 | OCH₃ | H | H | OCH₃ | —⟨C₆H₄⟩—⟨C₆H₄⟩— (biphenyl) | Y |
| A-18 | OCH₃ | H | H | OCH₃ | —⟨C₆H₄⟩— (1,4-phenylene) | YG |

-continued
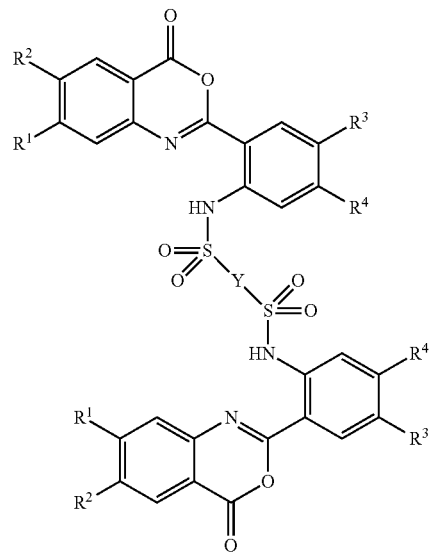
| Compound | R¹ | R² | R³ | R⁴ | Y | Fluorescence colour[4] |
|---|---|---|---|---|---|---|
| A-19 | OCH₃ | H | H | OCH₃ | -C₆H₄-SO₂-C₆H₄- | Y |
| A-20 | OCH₃ | H | H | OCH₃ | -C₆H₄-CO-C₆H₄- | Y |
| A-21 | OCH₃ | H | H | OCH₃ | -C₆H₄-CH₂-C₆H₄- | YG |
| A-22 | OCH₃ | H | H | OCH₃ | -C₆H₄-C(CH₃)₂-C₆H₄- | Y |
| A-23 | OCH₃ | H | H | OCH₃ | -C₆H₄-O-C₆H₄- | G—YG |
| A-24 | OCH₃ | H | H | OCH₃ | -C₆H₄-Y-C₆H₄-[1] | G—YG |
| A-25 | [2] | [2] | [3] | [3] | -C₆H₄-C₆H₄- | G |
| A-26 | [2] | [2] | [3] | [3] | -C₆H₄- | G |
| A-27 | [2] | [2] | [3] | [3] | -C₆H₄-SO₂-C₆H₄- | Y |

-continued
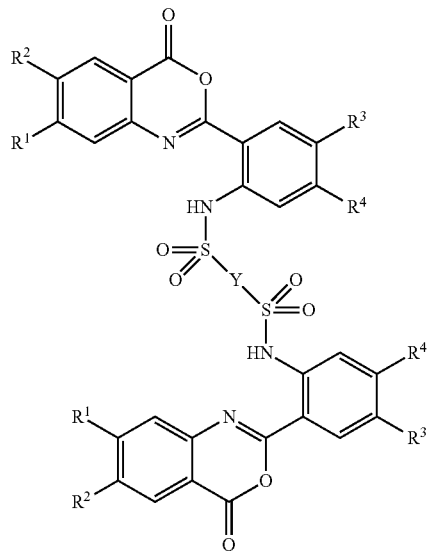
| Compound | R¹ | R² | R³ | R⁴ | Y | Fluorescence colour⁴⁾ |
|---|---|---|---|---|---|---|
| A-28 | 2) | 2) | 3) | 3) | -C₆H₄-C(=O)-C₆H₄- | Y |
| A-29 | 2) | 2) | 3) | 3) | -C₆H₄-CH₂-C₆H₄- | Y |
| A-30 | 2) | 2) | 3) | 3) | -C₆H₄-C(CH₃)₂-C₆H₄- | Y |
| A-31 | 2) | 2) | 3) | 3) | -C₆H₄-O-C₆H₄- | Y |
| A-32 | 2) | 2) | 3) | 3) | -C₆H₄-Y-C₆H₄- ¹⁾ | Y |
| A-33 | H | H | H | H | m-C₆H₄- | YG |
| A-34 | H | CH₃ | CH₃ | H | m-C₆H₄- | YG |
| A-35 | OCH₃ | H | H | OCH₃ | m-C₆H₄- | YG |

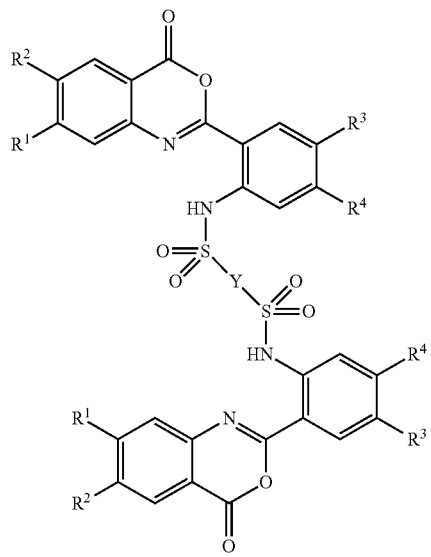

| Compound | R¹ | R² | R³ | R⁴ | Y | Fluorescence colour[4] |
|---|---|---|---|---|---|---|
| A-36 | [2] | [2] | [3] | [3] | (3,5-dimethylphenyl) | YG |

[1] Y is —O—CH$_2$CH$_2$—O—.

[2] R¹ and R² together form a group (fused benzene).

[3] R³ and R⁴ together form a group (fused benzene).

[4] G (green), Y (yellow), YG (yellow-green).

APPLICATION EXAMPLES

Application Example 1 (Printing)

A fluorescent offset ink is prepared containing 10.0 weight percent on solids of the compound A-2 from example 1. The ink is prepared on a 3-roll mill and comprises 10 weight percent of high tack varnish (CAS 68458-35-5, alkyd resin), 86.5 weight percent of a commercial offset varnish and 1 weight percent of a drying agent (based on CAS 136-52-7; cobalt bis (2-ethylhexanoate) and oleic acid, CAS 112-80-1). The ink is printed by an offset printing equipment to banknote paper. The print is visually almost colorless, but is shows green fluorescence under UV-light (365 nm). The print exhibits excellent light fastness and very good resistance against all types of solvents, acids, bases, hydrogen peroxide, hypochlorite, sodium sulfite, boiling water etc.

Comparative Application Example 1 (Printing)

By proceeding as indicated in Application Example 1, but using 2-(2-(2-naphtalenesulphonylamino)phenyl)-4H-3,1-benzoxazin-4-one (EP0314350) as fluorescent pigment with the structure indicated below, is likewise obtained a colorless offset print having excellent fastness to light.

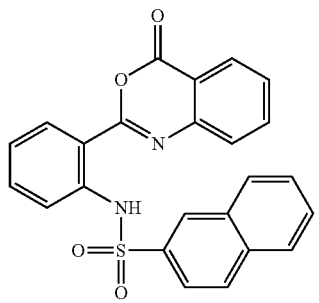 [SMILES: O=c1oc(-c2ccccc2NS(=O)(=O)c2ccc3ccccc3c2)nc2ccccc12]

Resistance against solvents like ethanol, white spirit, acids, bases, hydrogen peroxide synthetic sweat and detergents is excellent. But resistance against solvents like toluene, acetone, boiling water or against aggressive chemicals like hypochlorite is not sufficient for banknote printing.

For testing procedure cf. "Chemical and Physical Resistance" in "Extract of the ANNEX 13 of the Technical Specification for Euro banknote production" (European Central Bank; July 2004).

In the following Table the test results of the critical fastnesses are given for Application Example 1 and Comparative Application Example 1.

| Resistance against: | Application Example 1 | Comparative Application Example 1 |
|---|---|---|
| Acetone | 4 | 0 |
| Toluene | 4 | 0 |
| Ethylacetate | 4 | 0 |
| sope | 4 | 0 |

Evaluation by UV-Light (365 nm)
Ranking List According to the European Central Bank
4: no change or minor changes not visible with naked eyes
3: minor change
2: considerable change; less than 50% damaged
1: major change; more than 50% damaged
0: element disappeared

The invention claimed is:
1. A method of security printing, the method comprising:
contacting a compound with a substrate;
wherein said compound has a formula (I)

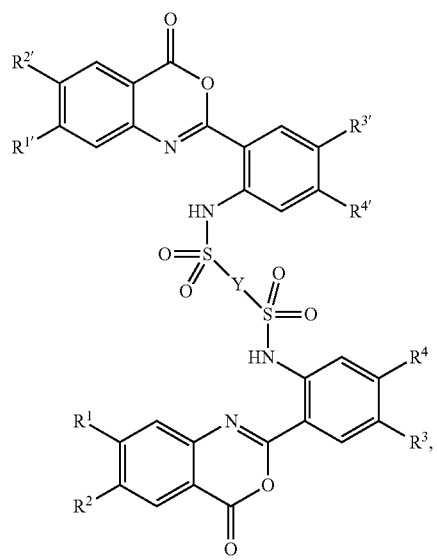

(I)

wherein
$R^1$ and $R^{1'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy;
$R^2$ and $R^{2'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy,
$R^3$ and $R^{3'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_8$alkoxy,
$R^4$ and $R^{4'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy, or one or more pairs of two substituents selected from the group consisting of $R^1$ and $R^2$, $R^{1'}$ and $R^{2'}$, $R^3$ and $R^4$, and $R^{3'}$ and $R^{4'}$ together form a group

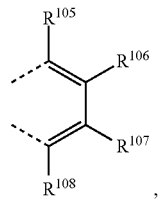

wherein
$R^{105}$, $R^{106}$, $R^{107}$ and $R^{108}$ are each independently H, $C_1$-$C_{18}$alkyl, $C_1$-$C_{18}$alkyl interrupted by —O—, $C_1$-$C_{18}$alkoxy, or $C_1$-$C_{18}$alkoxy interrupted by —O—, and
Y is a group of formula —$(Y^1)_{n1}$—$(Y^2)_{n2}$—$(Y^3)_{n3}$—,
wherein $Y^1$ and $Y^3$ are independently of each other a substituted, or unsubstituted arylene group having 6 to 10 ring carbon atoms, or a substituted or unsubstituted heteroarylene group having 3 to 9 ring carbon atoms,
$Y^2$ is —O—, —S—, —$NR^{12}$—, —$SO_2$—, —C(=O)—, —$(CR^8R^9)_{n4}$—, —O—$(CR^{10}R^{11})_{n5}$—O—, $R^8$ and $R^9$ are independently of each other H, or a $C_1$-$C_8$alkyl group,
$R^{10}$ and $R^{11}$ are independently of each other H, or a $C_1$-$C_8$alkyl group,
$R^{12}$ is H, or a $C_1$-$C_8$alkyl group, or a $C_6$-$C_{10}$aryl group,
n1 is 1, or 2, n2 is 0, or 1, n3 is 1, or 2, n4 is an integer of 1 to 4 and n5 is an integer of 1 to 4.

2. A method of improving a fastness property of a print, the method comprising:
contacting a printing ink formulation comprising a compound with a substrate;
wherein said compound has a formula (I)

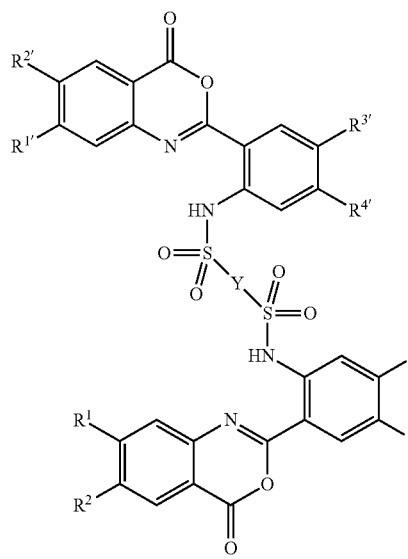

(I)

wherein
$R^1$ and $R^{1'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy;

$R^2$ and $R^{2'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy, $R^3$ and $R^{3'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy, $R^4$ and $R^{4'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy, or one or more pairs of two substituents selected from the group consisting of $R^1$ and $R^2$, $R^{1'}$ and $R^{2'}$, $R^3$ and $R^4$, and $R^{3'}$ and $R^{4'}$ together form a group

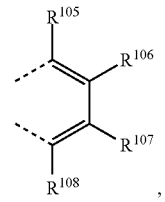

wherein $R^{105}$, $R^{106}$, $R^{107}$ and $R^{108}$ are each independently H, $C_1$-$C_{18}$alkyl, $C_1$-$C_{18}$alkyl interrupted by —O—, $C_1$-$C_{18}$alkoxy, or $C_1$-$C_{18}$alkoxy interrupted by —O—, and Y is a group of formula —$(Y^1)_{n1}$—$(Y^2)_{n2}$—$(Y^3)_{n3}$—, wherein $Y^1$ and $Y^3$ are independently of each other a substituted, or unsubstituted arylene group having 6 to 10 ring carbon atoms, or a substituted or unsubstituted heteroarylene group having 3 to 9 ring carbon atoms, $Y^2$ is —O—, —S—, —$NR^{12}$—, —$SO_2$—, —C(=O)—, —$(CR^8R^9)_{n4}$—, —O—$(CR^{10}R^{11})_{n5}$—O—, $R^8$ and $R^9$ are independently of each other H, or a $C_1$-$C_8$alkyl group, $R^{10}$ and $R^{11}$ are independently of each other H, or a $C_1$-$C_8$alkyl group, $R^{12}$ is H, or a $C_1$-$C_8$alkyl group, or a $C_6$-$C_{10}$aryl group, n1 is 1, or 2, n2 is 0, or 1, n3 is 1, or 2, n4 is an integer of 1 to 4 and n5 is an integer of 1 to 4.

3. A printing ink formulation, comprising:
a) at least one compound,
b) a polymeric binder,
c) a solvent,
d) optionally a colorant, and
e) optionally a further additive;

wherein said compound has a formula (I)

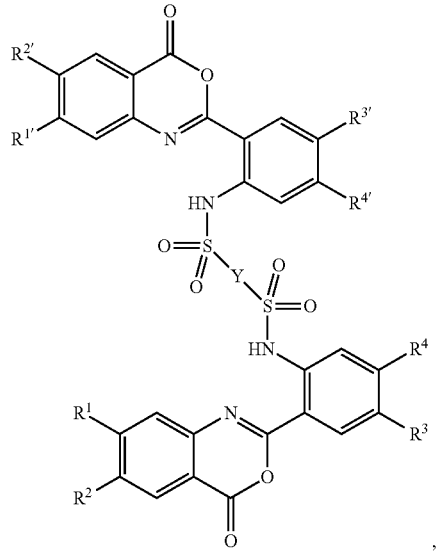

wherein $R^1$ and $R^{1'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy;

$R^2$ and $R^{2'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy, $R^3$ and $R^{3'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy, $R^4$ and $R^{4'}$ are each independently hydrogen, $C_1$-$C_{18}$alkyl, substituted $C_1$-$C_{18}$alkyl, $C_6$-$C_{24}$aryl, substituted $C_6$-$C_{24}$aryl, $C_6$-$C_{24}$heteroaryl, substituted $C_6$-$C_{24}$heteroaryl, halogen, or $C_1$-$C_{18}$alkoxy, or one or more pairs of two substituents selected from the group consisting of $R^1$ and $R^2$, $R^{1'}$ and $R^{2'}$, $R^3$ and $R^4$, and $R^{3'}$ and $R^{4'}$ together form a group

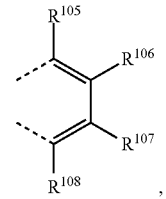

wherein $R^{105}$, $R^{106}$, $R^{107}$ and $R^{108}$ are each independently H, $C_1$-$C_{18}$alkyl, $C_1$-$C_{18}$alkyl interrupted by —O—, $C_1$-$C_{18}$alkoxy, or $C_1$-$C_{18}$alkoxy interrupted by —O—, and Y is a group of formula —$(Y^1)_{n1}$—$(Y^2)_{n2}$—$(Y^3)_{n3}$—, wherein $Y^1$ and $Y^3$ are independently of each other a substituted, or unsubstituted arylene group having 6 to 10 ring carbon atoms, or a substituted or unsubstituted heteroarylene group having 3 to 9 ring carbon atoms, $Y^2$ is —O—, —S—, —NR$^{12}$—, —SO$_2$—, —C(=O)—, —(CR$^8$R$^9$)$_{n4}$—, —O—(CR$^{10}$R$^{11}$)$_{n5}$—O—, R$^8$ and R$^9$ are independently of each other H, or a C$_1$-C$_8$alkyl group, R$^{10}$ and R$^{11}$ are independently of each other H, or a C$_1$-C$_8$alkyl group, R$^{12}$ is H, or a C$_1$-C$_8$alkyl group, or a C$_6$-C$_{10}$aryl group, n1 is 1, or 2, n2 is 0, or 1, n3 is 1, or 2, n4 is an integer of 1 to 4 and n5 is an integer of 1 to 4.

4. The printing ink formulation of claim 3, comprising
a) 0.0001 to 25% by weight of the compound,
b) 5 to 74% by weight of the polymeric binder,
c) 1 to 94.9999% by weight of the solvent,
d) 0 to 25% by weight of the colorant, and
e) 0 to 25% by weight of the further additive,
wherein the sum of components a) to e) is 100%.

5. A security document, comprising:
a substrate and a compound of
formula (I)

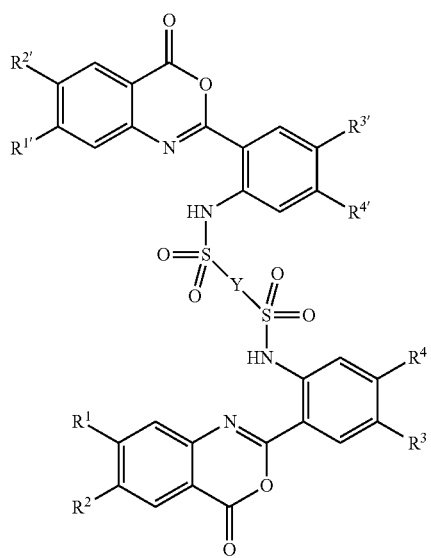

wherein
R$^1$ and R$^{1'}$ are each independently hydrogen, C$_1$-C$_{18}$alkyl, substituted C$_1$-C$_{18}$alkyl, C$_6$-C$_{24}$aryl, substituted C$_6$-C$_{24}$aryl, C$_6$-C$_{24}$heteroaryl, substituted C$_6$-C$_{24}$heteroaryl, halogen, or C$_1$-C$_{18}$alkoxy;

R$^2$ and R$^{2'}$ are each independently hydrogen, C$_1$-C$_{18}$alkyl, substituted C$_1$-C$_{18}$alkyl, C$_6$-C$_{24}$aryl, substituted C$_6$-C$_{24}$aryl, C$_6$-C$_{24}$heteroaryl, substituted C$_6$-C$_{24}$heteroaryl, halogen, or C$_1$-C$_{18}$alkoxy, R$^3$ and R$^{3'}$ are each independently hydrogen, C$_1$-C$_{18}$alkyl, substituted C$_1$-C$_{18}$alkyl, C$_6$-C$_{24}$aryl, substituted C$_6$-C$_{24}$aryl, C$_6$-C$_{24}$heteroaryl, substituted C$_6$-C$_{24}$heteroaryl, halogen, or C$_1$-C$_{18}$alkoxy, R$^4$ and R$^{4'}$ are each independently hydrogen, C$_1$-C$_{18}$alkyl, substituted C$_1$-C$_{18}$alkyl, C$_6$-C$_{24}$aryl, substituted C$_6$-C$_{24}$aryl, C$_6$-C$_{24}$heteroaryl, substituted C$_6$-C$_{24}$heteroaryl, halogen, or C$_1$-C$_{18}$alkoxy, or one or more pairs of two substituents selected from the group consisting of R$^1$ and R$^2$, R$^{1'}$ and R$^{2'}$, R$^3$ and R$^4$, and R$^{3'}$ and R$^{4'}$ together form a group

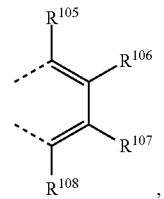

wherein
R$^{105}$, R$^{106}$, R$^{107}$ and R$^{108}$ are each independently H, C$_1$-C$_{18}$alkyl, C$_1$-C$_{18}$alkyl interrupted by —O—, C$_1$-C$_{18}$alkoxy, or C$_1$-C$_{18}$alkoxy interrupted by —O—, and Y is a group of formula —(Y$^1$)$_{n1}$—(Y$^2$)$_{n2}$—(Y$^3$)$_{n3}$—,
wherein Y$^1$ and Y$^3$ are independently of each other a substituted, or unsubstituted arylene group having 6 to 10 ring carbon atoms, or a substituted or unsubstituted heteroarylene group having 3 to 9 ring carbon atoms, Y$^2$ is —O—, —S—, —NR$^{12}$—, —SO$_2$—, —(CR$^8$R$^9$)$_{n4}$—, —O—(CR$^{10}$R$^{11}$)$_{n5}$—O—, R$^8$ and R$^9$ are independently of each other H, or a C$_1$-C$_8$alkyl group, R$^{10}$ and R$^{11}$ are independently of each other H, or a C$_1$-C$_8$alkyl group, R$^{12}$ is H, or a C$_1$-C$_8$alkyl group, or a C$_6$-C$_{10}$aryl group, n1 is 1, or 2, n2 is 0, or 1, n3 is 1, or 2, n4 is an integer of 1 to 4 and n5 is an integer of 1 to 4.

6. A security document, obtained by a printing process comprising contacting the printing ink formulation of claim 3 with a substrate.

7. The security document of claim 5, which is a bank note, a passport, a check, a voucher, an ID- or transaction card, a stamp or a tax label.

8. The method of claim 1, wherein the group of formula —(Y$^1$)$_{n1}$—(Y$^2$)$_{n2}$—(Y$^3$)$_{n3}$— is at least one selected from the group consisting of

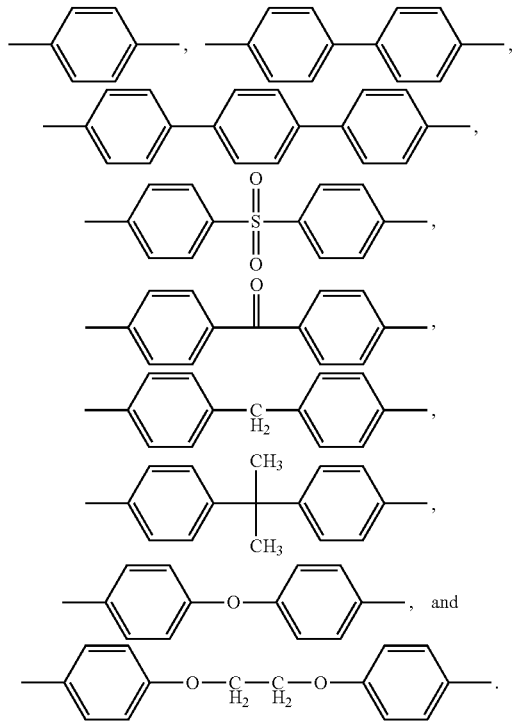

9. The method of claim 2, wherein the group of formula —$(Y^1)_{n1}$—$(Y^2)_{n2}$—$(Y^3)_{n3}$— is at least one selected from the group consisting of

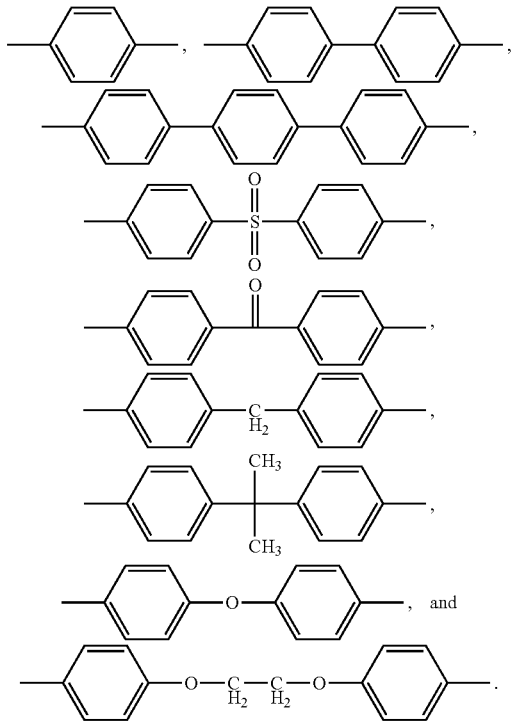

10. The printing ink formulation of claim 3, wherein the group of formula —$(Y^1)_{n1}$—$(Y^2)_{n2}$—$(Y^3)_{n3}$— is at least one selected from the group consisting of

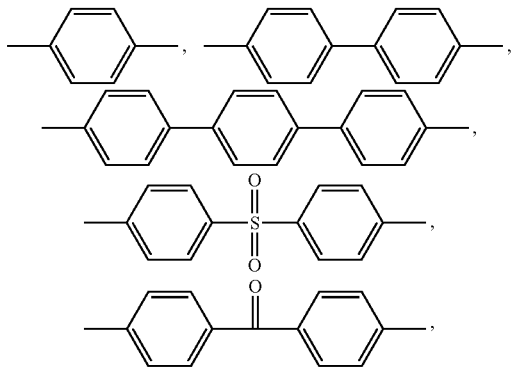

11. The security document of claim 5, wherein the group of formula —$(Y^1)_{n1}$—$(Y^2)_{n2}$—$(Y^3)_{n3}$— is at least one selected from the group consisting of

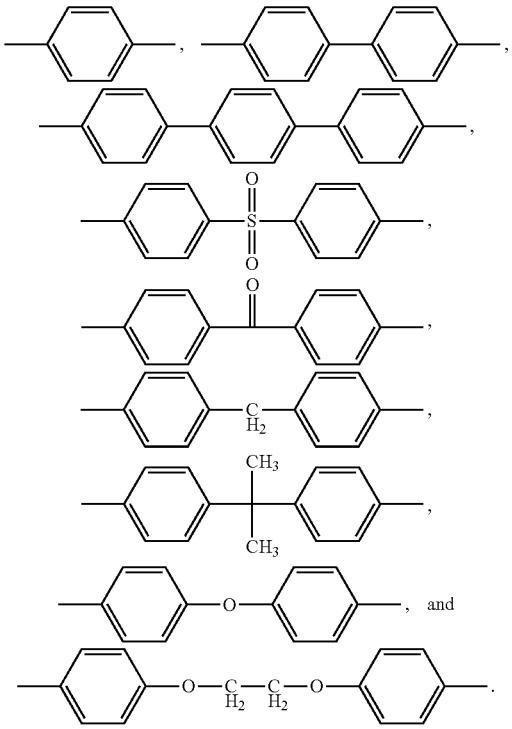

* * * * *